United States Patent [19]

Mikkelsen

[11] Plant 4,211

[45] Feb. 7, 1978

[54] BEGONIA PLANT

[75] Inventor: James C. Mikkelsen, Ashtabula, Ohio

[73] Assignee: Mikkelsens, Inc., Ashtabula, Ohio

[21] Appl. No.: 769,843

[22] Filed: Feb. 17, 1977

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Donald D. Jeffery

[57] ABSTRACT

A begonia cultivar having light pink tepals giving the appearance of azalea blossoms.

1 Drawing Figure

The present invention relates to a new and distinctive cultivar of begonia plant, botanically known as *begonia elatior* (hiemalis-Fotsch) and known by the cultivar name Pink Fantasy.

The new cultivar was discovered by me as a mutation of Fantasy and was observed in a group of flowering 4 inch stock plants of the parent cultivar. Fantasy is disclosed in my issued U.S. Plant Pat. No. 3,911, granted June 15, 1976. Asexual reproduction by stem and/or leaf cuttings of the new cultivar has reproduced the unique features of the new cultivar through successive propagations.

The following characteristics distinguish Pink Fantasy from both its parents and other begonias commercially known and used in the floriculture industry:

1. The flowers of Pink Fantasy are light pink as compared to the deep rose red flower color of the parent cultivar Fantasy.

2. Pink Fantasy has similar keeping qualities to Fantasy, being much greater than Rieger Aphrodite types.

3. The plant habit of Pink Fantasy is upright but growth is slower and more compact than Rieger Schwabenland types.

4. Flower form and placement against the foliage background gives Pink Fantasy the appearance of an azalea. Flowers are slightly smaller than those of Fantasy.

5. Pink Fantasy propagates very well from leaf cuttings but propagation is generally 7 to 14 days slower than for Schwabenland types.

6. Although Pink Fantasy is most valuable as an upright pot plant begonia, it can be used as a hanging basket when properly cultivated for that purpose.

7. Like Fantasy, the mutant has the same resistance to powdery mildew.

8. Since Pink Fantasy encompasses the same overall high quality and appearance of Fantasy it has the comparable potential of adding to the economic value of elatior begonias for commercial flowering pot plant production.

The accompanying colored photograph illustrates the new cultivar and shows the colors as true as it is reasonably possible to obtain in a colored reproduction of this type.

The following is a detailed description of my new begonia cultivar based on plants produced under commercial practices in the greenhouses of Mikkelsens Inc., Ashtabula, Ohio. Color references are made to the Royal Horticultural Society Colour Chart except where general color terms of ordinary dictionary significance are used.

Parentage: A spontaneous mutation of the elatior begonia Fantasy, described in my U.S. Plant Pat. No. 3,911.

Propagation: Is most satisfactory by leaf cuttings that root in approximately 35 days at 22° C. Basal adventitious buds are formed at the base of the leaf petiole and subsequently develop into shoots emerging above the propagating media in a 5 cm. pot in an additional 45 days in the summer to 80 days in the winter under the conditions at Ashtabula, Ohio.

Rooting habit: Rooting and shooting is considered slower than for Schwabenland types but roots are quite profuse, fine, and dendritic.

Plant form: Upright and bushy when produced from leaf cuttings.

Habit of growth: Compact, slow growing, close internodes, with good self branching habit.

Blooming habits: Free flowering, closely clustered double flowers, produced over a long period of time, with excellent keeping qualities. Flowering response is quite uniform throughout the year.

Blooming season: Flowering is generally more profuse in the fall and spring months. Modern propagation and cultural techniques can increase flower quantity for both winter and summer.

Foliage: Foliage is above average in quantity and appearance because of close internodes and considerable self branching.

*Size.*—Mature leaves under normal cultural practices in Ohio are approximately 8 cm. wide by 8 cm. long with short petioles up to 2 cm. long.

*Shape.*—Nearly round, flat, very little cupping.

*Texture.*—Smooth, waxy, rigid, crisp, thick.

*Margin.*—Very small serrations to nearly complete.

*Color.*—Young foliage, upper — near 146A, lower areas between veins reddish brown. Mature foliage — upper; darker than green 139-A, lower; dark dull red, veins extremely protruding.

Disease resistance: In testing with Fantasy in highly infected areas of mildew Pink Fantasy shows the same immunity. To date indications are that the cultivar is also quite resistant to *Xanthomonas begoniae.*

Flowers:

*Borne.*—On a compound raceme, clustered, with short pedicels keeping the flowers close to the leaf canopy.

*Quantity.*—Appears to be above average since there is considerable self branching to allow for more flowering points.

*Buds.*—Flat and approximately 8 to 10 mm. in diameter prior to opening. Flowers approaching maturity measure up to 5 cm. in diameter.

*Tepals.*—Red 52B-C fading to 52D.

*Reproductive Organs.*—Elatior begonias are generally considered sterile. Stamens: None seen to date. Pollen: None seen to date. Styles/Ovaries: None seen to date.

I claim:

1. A new and distinct cultivar of begonia plant known by the cultivar name Pink Fantasy and particularly characterized as to uniqueness by the combined characteristics of light pink flower color, excellent keeping qualities; upright, compact and relatively slow growth habit; excellent appearance due to flower form and placement against the foliage background; good propagation from leaf cuttings, and by its resistance to disease.

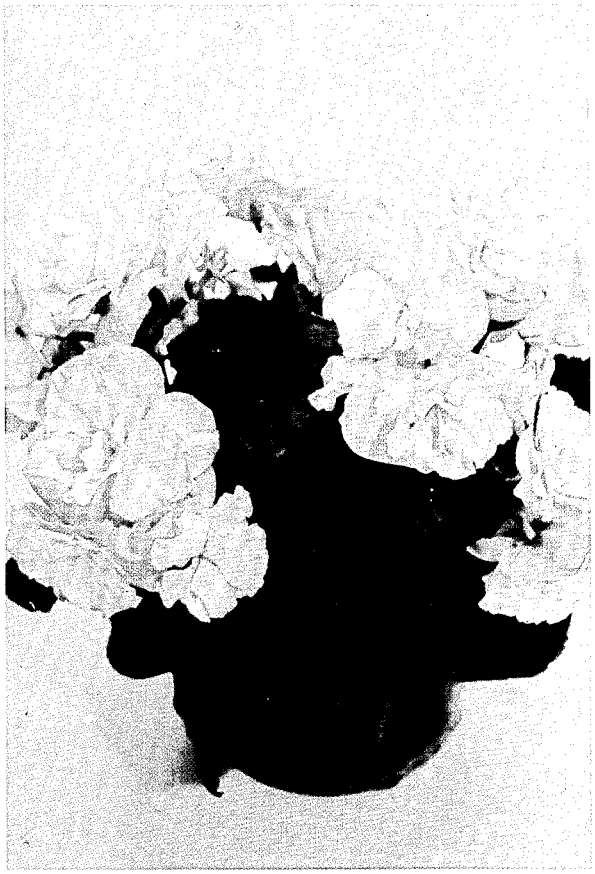

* * * * *